United States Patent
Fonger et al.

(10) Patent No.: US 6,497,698 B1
(45) Date of Patent: Dec. 24, 2002

(54) METHOD AND APPARATUS FOR TREATING A PATIENT

(75) Inventors: James Fonger, Tacoma Park, MD (US); James A. Magovern, Pittsburgh, PA (US); Wayne P. Griffin, Cranberry, PA (US); Richard E. Davis, Grand Rapids, MI (US)

(73) Assignee: Cardiac Assist, Inc., Pittsburgh, PA (US)

( * ) Notice: Subject to any disclaimer, the term of this patent is extended or adjusted under 35 U.S.C. 154(b) by 0 days.

(21) Appl. No.: 09/315,618

(22) Filed: May 20, 1999

(51) Int. Cl.$^7$ ............................................... A61M 31/00
(52) U.S. Cl. ..................... 604/508; 604/8; 604/164.13; 604/523
(58) Field of Search ................................. 604/523, 529, 604/541, 95.02, 164.08, 8, 9, 500, 506, 507, 508, 510, 164.13

(56) References Cited

U.S. PATENT DOCUMENTS

| | | | |
|---|---|---|---|
| 4,137,906 A | | 2/1979 | Akiyama et al. |
| 4,342,313 A | | 8/1982 | Chittenden |
| 4,790,825 A | | 12/1988 | Bernstein et al. |
| 5,190,528 A | | 3/1993 | Fonger et al. |
| 5,314,418 A | * | 5/1994 | Takano et al. .............. 604/525 |
| 5,449,342 A | * | 9/1995 | Hirose et al. ................. 600/16 |
| 5,824,071 A | * | 10/1998 | Nelson et al. ................. 604/8 |
| 5,928,269 A | * | 7/1999 | Alt ................................ 607/5 |
| 6,033,413 A | | 3/2000 | Mikus et al. |
| 6,138,043 A | * | 10/2000 | Avitall ........................ 600/377 |
| 6,308,091 B1 | * | 10/2001 | Avitall ........................ 600/374 |
| 6,328,699 B1 | * | 12/2001 | Eigler et al. ................ 600/485 |

OTHER PUBLICATIONS

A. Pavie, PH. Leger, A. Nzomvuama, J. Szefner, M. Regan, E. Vaissier, and I. Gandjbakhch, "Left Centrifugal Pump Cardiac Assist with Transseptal Percutaneous Left Atrial Cannula", *Artificial Organs,* 22(6):502–507, Blackwell Science, Inc., 1998 International Society for Artificial Organs.

* cited by examiner

Primary Examiner—Brian L. Casler
Assistant Examiner—Jeremy Thissell
(74) Attorney, Agent, or Firm—Ansel M. Schwartz

(57) ABSTRACT

An apparatus for treating a patient. The apparatus includes a catheter having a distal end and a proximal end. The distal end has an orifice through which a fluid can flow. The distal end has a port through which the fluid can flow. The port is adjacent to but apart from the orifice. The apparatus includes a mechanism for controlling the size of the port that is open. The controlling mechanism is disposed over the port and able to close the port. An apparatus for treating a patient. The apparatus includes a catheter having a proximal end and a distal end having an orifice through which a fluid can flow. The distal end has an end marker disposed about the orifice which appears in an image of an imaging device. An apparatus for treating a patient. The apparatus includes a catheter having a proximal end and a distal end having an orifice through which fluid can flow. The catheter has an axis. The distal end has a plurality of holes having an elongate shape disposed essentially in parallel with the axis of the catheter with smooth edges so blood cells are not damaged as they pass through the holes. A method for treating a patient. The method includes the steps of inserting a catheter in a vessel. Then there is the step of opening a port in the catheter disposed adjacent an orifice in the distal end of the catheter so blood can flow through the port and the orifice.

13 Claims, 5 Drawing Sheets

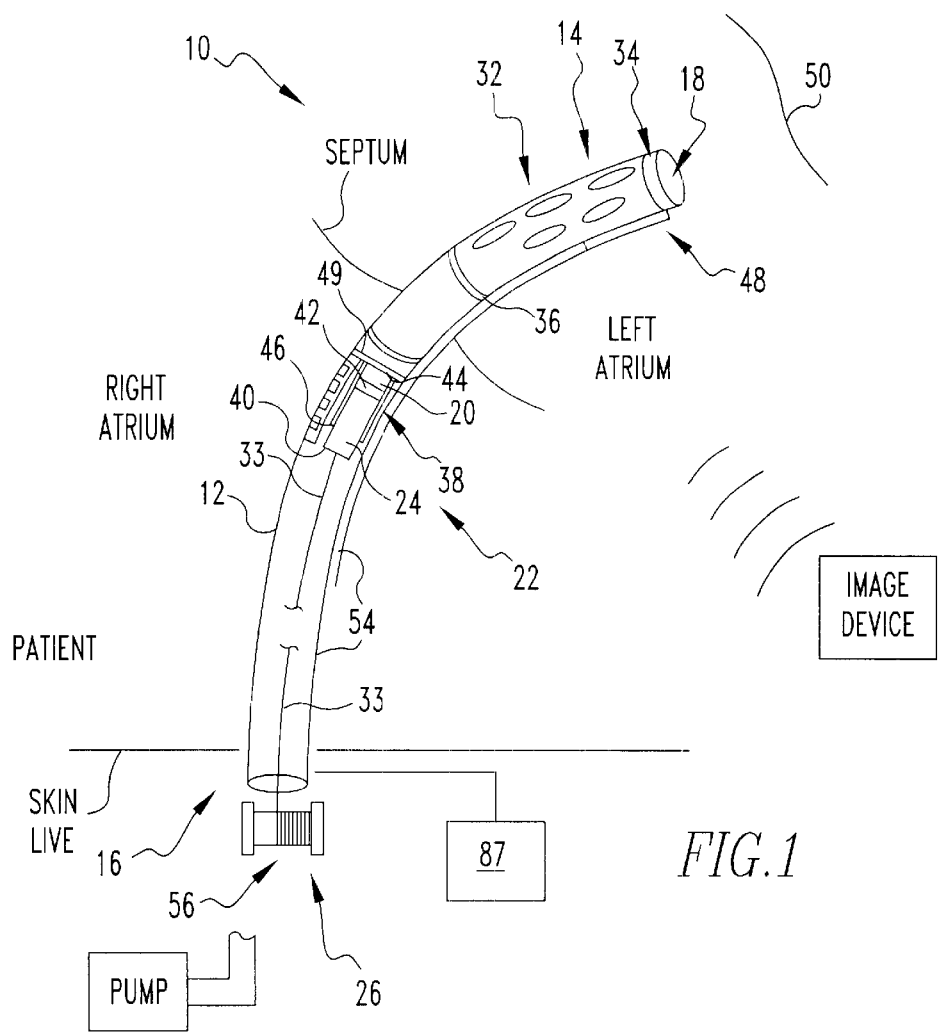
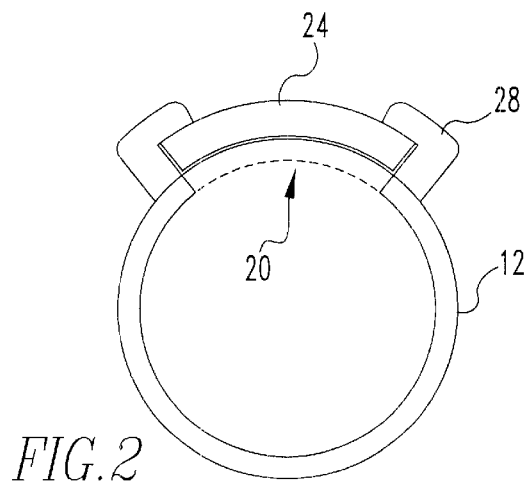

METHOD AND APPARATUS FOR TREATING A PATIENT

FIELD OF THE INVENTION

The present invention is related to a transseptal cannula. More specifically, the present invention is related to a transseptal cannula having a-port and an orifice where the orifice can access the left atrium of the heart and the port can access the right atrium of the heart.

BACKGROUND OF THE INVENTION

For temporary and particularly emergency problems such as surgery, or holding a potential transplant patient until a natural heart is available, there is a need for simple equipment in a hospital that can be quickly connected to the patient without surgical intervention and that can provide bypass time to the patient.

The present invention provides for a quick and a relatively simple way for providing assistance to the heart and its operation. The present invention allows for the access of the left atrium as well as the right atrium simultaneously, or separately, depending on the needs of the patient and the determinations of the physician.

SUMMARY OF THE INVENTION

An apparatus for treating a patient. The apparatus comprises a catheter having a distal end and a proximal end. The distal end has an orifice through which a fluid can flow. The distal end has a port through which the fluid can flow. The port is adjacent to but apart from the orifice. The apparatus comprises a mechanism for controlling the size of the port that is open. The controlling mechanism is disposed over the port and able to close the port.

An apparatus for treating a patient. The apparatus comprises a catheter having a proximal end and a distal end having an orifice through which a fluid can flow. The distal end has an end marker disposed about the orifice which appears in an image of an imaging device.

An apparatus for treating a patient. The apparatus comprises a catheter having a proximal end and a distal end having an orifice through which fluid can flow. The catheter has an axis. The distal end has a plurality of holes having an elongate shape disposed essentially in parallel with the axis of the catheter with smooth edges so blood cells are not damaged as they pass through the holes.

A method for treating a patient. The method comprises the steps of inserting a catheter in a vessel. Then there is the step of opening a port in the catheter disposed adjacent an orifice in the distal end of the catheter so blood can flow through the port and the orifice.

The present invention pertains to a method for accessing the heart of a patient. The method comprises the steps of inserting a guide wire into a vessel of a patient to a right atrium of the heart. Then there is the step of threading the guide wire through an orifice of a catheter. Next there is the step of moving the catheter with a needle disposed in the catheter along the guide wire to the right atrium so only the needle and guide wire and catheter are in the vessel and the needle and guide wire are simultaneously in the catheter. Then there is the step of moving the guide wire out of the orifice but keeping the guide wire in the catheter simultaneously with the needle. Next there is the step of moving the needle through the orifice. Then there is the step of puncturing a septum of the heart with the needle and catheter and moving the catheter into a left atrium of the heart. Next there is the step of removing the needle and guide wire from the catheter.

The present invention pertains to a method for accessing the heart of a patient. The method comprises the steps of inserting a guide wire into a vessel of a patient to a right atrium of the heart. Then there is the step of threading the guide wire through an orifice of a catheter. Next there is the step of moving the catheter with a needle disposed in the catheter along the guide wire to the right atrium. Then there is the step of moving a needle into the catheter so only the needle and guide wire and catheter are in the vessel and the needle and guide wire are simultaneously in the catheter. Next there is the step of moving the guide wire out of the orifice. Then there is the step of moving the needle through the orifice. Next there is the step of puncturing a septum of the heart with the needle and catheter and moving the catheter into a left atrium of the heart. Then there is the step of removing the needle from the catheter.

BRIEF DESCRIPTION OF THE DRAWINGS

In the accompanying drawings, the preferred embodiment of the invention and preferred methods of practicing the invention are illustrated in which:

FIG. 1 is a schematic representation of an apparatus of the present invention.

FIG. 2 is a schematic representation of a cross-sectional view of a panel on a catheter.

DETAILED DESCRIPTION

Figure 3:
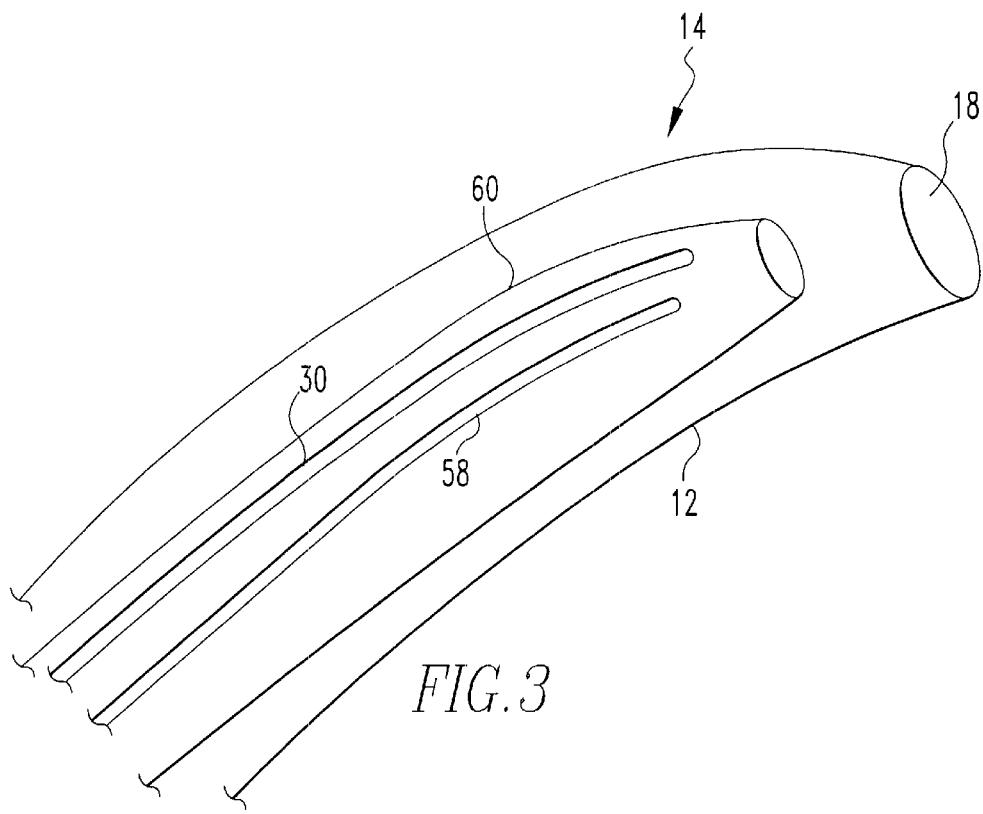
FIG. 3 is a schematic representation of a needle and wire in a second catheter in a cannula.

Referring now to the drawings wherein like reference numerals refer to similar or identical parts throughout the several views, and more specifically to FIGS. 1, 2 and 3 thereof, there is shown an apparatus 10 for treating a patient. The apparatus 10 comprises a catheter 12 having a distal end 14 and a proximal end 16. The distal end 14 has an orifice 18 through which a fluid can flow. The distal end 14 has a port 20 through which the fluid can flow. The port 20 is adjacent to but apart from the orifice 18. The apparatus 10 comprises a mechanism 22 for controlling the size of the port 20 that is open. The controlling mechanism 22 is disposed over the port 20 and able to close the port 20.

Preferably, the controlling mechanism 22 is able to fluidically seal the port 20. The controlling mechanism 22 preferably includes a panel 24 and a mechanism 26 for moving the panel 24. The panel 24 is in movable relationship with the moving mechanism 26. The moving mechanism 26 contacts the catheter 12 and is disposed about the port 20 so the panel 24 can be moved by the moving mechanism 26 to control the size of the port 20 that is open.

Preferably, the controlling mechanism 22 includes a frame 28 contacting the catheter 12 and positioned about the port 20. The panel 24 is disposed in the frame 28. The controlling mechanism 22 preferably includes a panel wire 33 connected to the panel 24 and extending along the catheter 12. Movement of the panel wire 33 causes movement of the panel 24.

Preferably, the distal end 14 has holes 32 through which fluid can flow disposed between the orifice 18 and the port 20. The holes 32 have an elongate shape and are disposed essentially in parallel with the longitudinal axis of the catheter 12.

The distal end 14 preferably has an end marker 34 disposed about the orifice 18. Preferably, the distal end 14 has a second marker 36 disposed between the port 20 and the holes 32. The panel 24 preferably has a front end 38 and a back end 40. The panel 24 has a first marker 42 disposed at the front end 38. Preferably, the port 20 has a front 44 and a back 46. The distal end 14 has a front port marker 49 disposed at the front 44 of the port 20.

The apparatus 10 preferably includes a stop 48 disposed about the distal end 14 which prevents the distal end 14 from puncturing an atrium wall 50. Preferably, the stop 48 has an expanded state and a compacted state. The stop 48 preferably includes a balloon 52 disposed about the distal end 14 and an inflation tube 54 which extends from the balloon 52 along the catheter 12. Preferably, the moving mechanism 26 includes a wheel hub 56 disposed at the proximal end 16 and connected to the wire 30 which moves the wire 30 when it is moved.

Preferably, the apparatus 10 includes a guide wire 30 which is disposed in the catheter 12, and a needle 58 which is disposed in the catheter 12. The apparatus 10 preferably includes a second catheter 60 which is disposed in the catheter 12 and in which the guide wire 30 and the needle 58 are disposed. The catheter 12 is preferably a cannula 12. An example of the placement of the cannula, second catheter 60, needle 58 and guide wire 30 in the right and left atrium of a patient is described in U.S. Pat. Nos. 5,190,528 and 4,790,825, both of which are incorporated by reference herein.

The present invention pertains to an apparatus 10 for treating a patient. The apparatus 10 comprises a catheter 12 having a proximal end 16 and a distal end 14 having an orifice 18 through which a fluid can flow. The distal end 14 has an end marker 34 disposed about the orifice 18 which appears in an image of an imaging device. Preferably, the marker is radio opaque. The imaging device can be one of many standard types of imaging devices available in the marketplace and well known to one skilled in the art.

The present invention pertains to an apparatus 10 for treating a patient. The apparatus 10 comprises a catheter 12 having a proximal end 16 and a distal end 14 having an orifice 18 through which fluid can flow. The catheter 12 has an axis. The distal end 14 has a plurality of holes 32 having an elongate shape disposed essentially in parallel with the axis of the catheter 12 with smooth edges so blood cells are not damaged as they pass through the holes 32.

Figure 4:
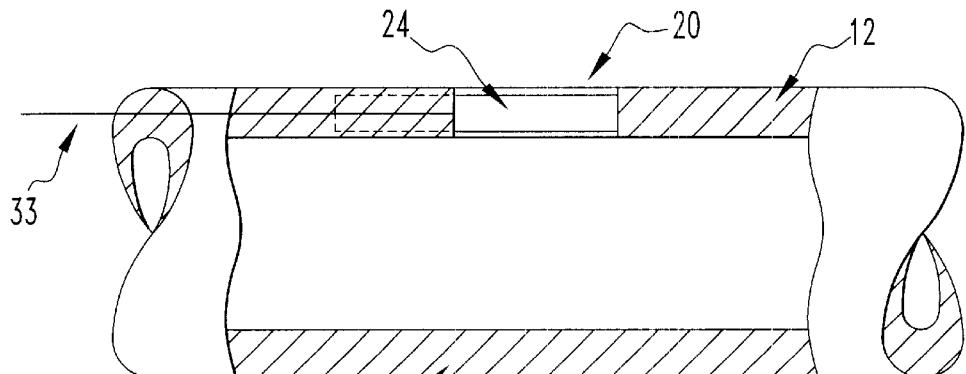
FIG. 4 is a schematic representation of a panel over a port of a cannula.
Figure 5:
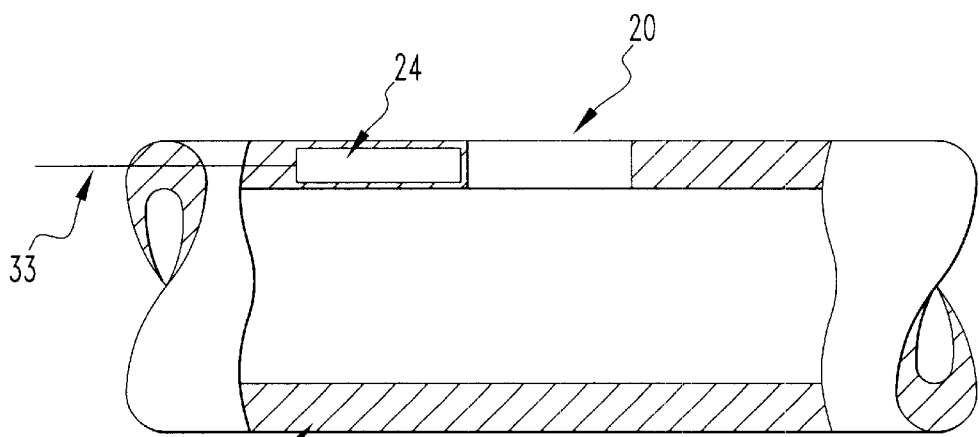
FIG. 5 is a schematic representation of a panel retracted from the port of a cannula.

The present invention pertains to a method for treating a patient. The method comprises the steps of inserting a catheter 12 in a vessel. Then there is the step of opening a port 20 in the catheter 12 disposed adjacent an orifice 18 in the distal end 14 of the catheter 12 so blood can flow through the port 20 and the orifice 18, as shown in FIGS. 4 and 5.

Preferably, the inserting step includes the step of inserting the distal end 14 of the catheter 12 with the orifice 18 into the left atrium while the port 20 is disposed in the right atrium. The opening step preferably includes the step of moving a panel 24 over the port 20 to open the port 20. Preferably, the inserting step includes the step of imaging an end marker 34 about the orifice 18 on the catheter 12 to identify the location of the orifice 18 in the patient.

The present invention pertains to a method for accessing the heart of a patient. The method comprises the steps of inserting a guide wire into a vessel of a patient to a right atrium of the heart. Then there is the step of threading the guide wire through an orifice of a catheter. Next there is the step of moving the catheter with a needle disposed in the catheter along the guide wire to the right atrium so only the needle and guide wire and catheter are in the vessel and the needle and guide wire are simultaneously in the catheter. Then there is the step of moving the guide wire out of the orifice but keeping the guide wire in the catheter simultaneously with the needle. Next there is the step of moving the needle through the orifice. Then there is the step of puncturing a septum of the heart with the needle and catheter and moving the catheter into a left atrium of the heart. Next there is the step of removing the needle and guide wire from the catheter.

The present invention pertains to a method for accessing the heart of a patient. The method comprises the steps of inserting a guide wire into a vessel of a patient to a right atrium of the heart. Then there is the step of threading the guide wire through an orifice of a catheter. Next there is the step of moving the catheter with a needle disposed in the catheter along the guide wire to the right atrium. Then there is the step of moving a needle into the catheter so only the needle and guide wire and catheter are in the vessel and the needle and guide wire are simultaneously in the catheter. Next there is the step of moving the guide wire out of the orifice. Then there is the step of moving the needle through the orifice. Next there is the step of puncturing a septum of the heart with the needle and catheter and moving the catheter into a left atrium of the heart. Then there is the step of removing the needle from the catheter.

In the operation of the invention, and referring to FIGS. 1, 2 and 3, the distal end 14 of the catheter 12, preferably a cannula 12, is inserted into a patient and moves to the right atrium of the patient's heart via the femoral vein, as is well known in the art. Generally, this occurs in the following way. The guide wire 30 is introduced into the patient and threaded to the right atrium of the patient. The cannula 12, the second catheter 60 (with the needle 58 disposed in the second catheter 60) are placed over the end of the guide wire 30 extending from the patient via the orifice 18 and the opening in the second catheter 60. The cannula 12 and second catheter 60, with the needle 58 inside the second catheter 60, are then inserted and moved along the guide wire 30 to the right atrium of the patient. When the distal end 14 of the cannula 12 is in the right atrium, the guide wire 30 is pulled back 46 into the cannula 12 freeing the orifice 18 so there is nothing in the orifice 18. The needle 58 is then advanced, as is the second catheter 60 through the orifice 18 so the second catheter 60 extends through the orifice 18 of the cannula 12 and the needle 58 extends through the opening of the second catheter 60. The needle 58 and second catheter 60 are then forced into the septum until they puncture the septum and move into the left atrium. The needle 58 is then retracted from the opening of the second catheter 60 and the guide wire 30 is moved forward through the second catheter's opening into the left atrium. The second catheter 60 is maintained in position while the guide wire 30 is maintained in place in the left atrium. The cannula 12 is then advanced forward into the left atrium along the guide wire 30 and the second catheter 60 which extend through the orifice 18. The presence of the second catheter 60 acts as a stiffener for the cannula 12 to assist in the placement of the cannula 12 in the left atrium. The second catheter 60, needle 58 and guide wire 30 are then removed from the cannula.

It should be noted that the aforementioned procedure can be performed without the cannula 12. Instead, the second catheter 60 acts with a dual purpose, as cannula 12 and the second catheter 60. In this case, the needle 58 and guide wire 30 are together disposed in the second catheter 60, and the cannula 12 is not present. When the second cannula 60 and needle 58 puncture the septum and move into the left atrium, the second catheter 60 remains in place and the guide wire 30 and the needle 58 are removed to clear a blood flow passage through the second catheter 60. This apparatus of second catheter 60, guide wire 30 and needle 58, without any of the other features described herein on the cannula 12, or with some or all of them, in and of itself can be used to access the left atrium. Again, the advantage of the combination of elements, is that it can serve to access the left atrium without having to take turns pulling the guide wire 30 out and then inserting the needle 58 into the second catheter 60 since the guide wire 30 and the needle 58 are together present in the second catheter 60 simultaneously; and the second catheter 60 serves a dual purpose of being the cannula 12 and second catheter 60, without needing the cannula 12. Alternatively, the needle can be inserted into the second catheter 60 after the second catheter has reached the right atrium.

During the process of moving the cannula 12 to the right atrium, removing the guide wire 30 from the orifice 18 and extending the needle through the orifice 18, an imaging device, external to the patient is imaging the location of the orifice 18 (and during the entire procedure) by noting where an end marker 34, disposed about the orifice 18, is located in the patient. Such an imaging system, for instance with the end marker 34 being radio opaque, is well known in the art. If it is desired, the guide wire 30 or a portion thereof, such as the tip of the guide wire 30, and/or the needle 58 or a portion thereof, such as the tip of the needle 58, can also be enhanced for imaging purposes, for example by having a radio opaque material, so the guide wire 30 and needle 58 can also be followed as they move through the patient.

Figure 6:
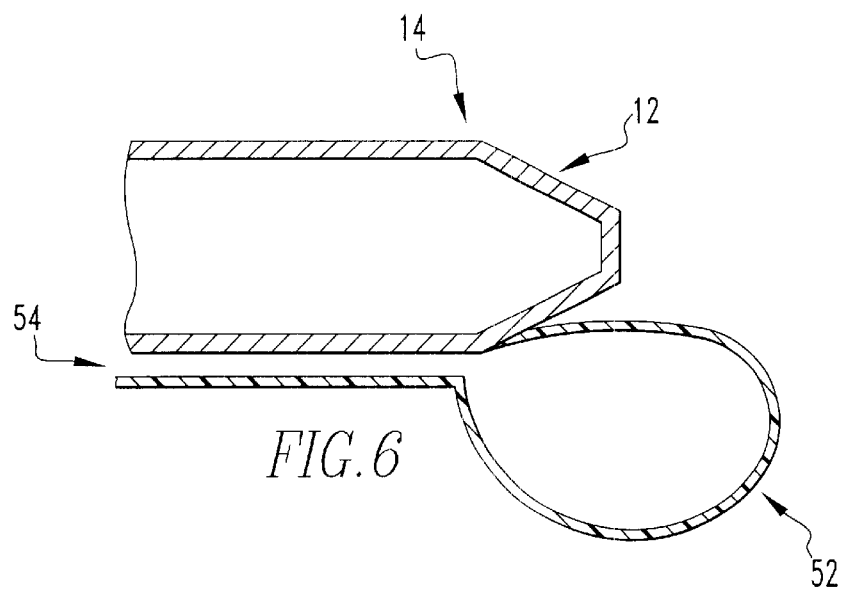
FIG. 6 is a schematic representation of a balloon catheter at the distal end of the cannula.
Figure 12:
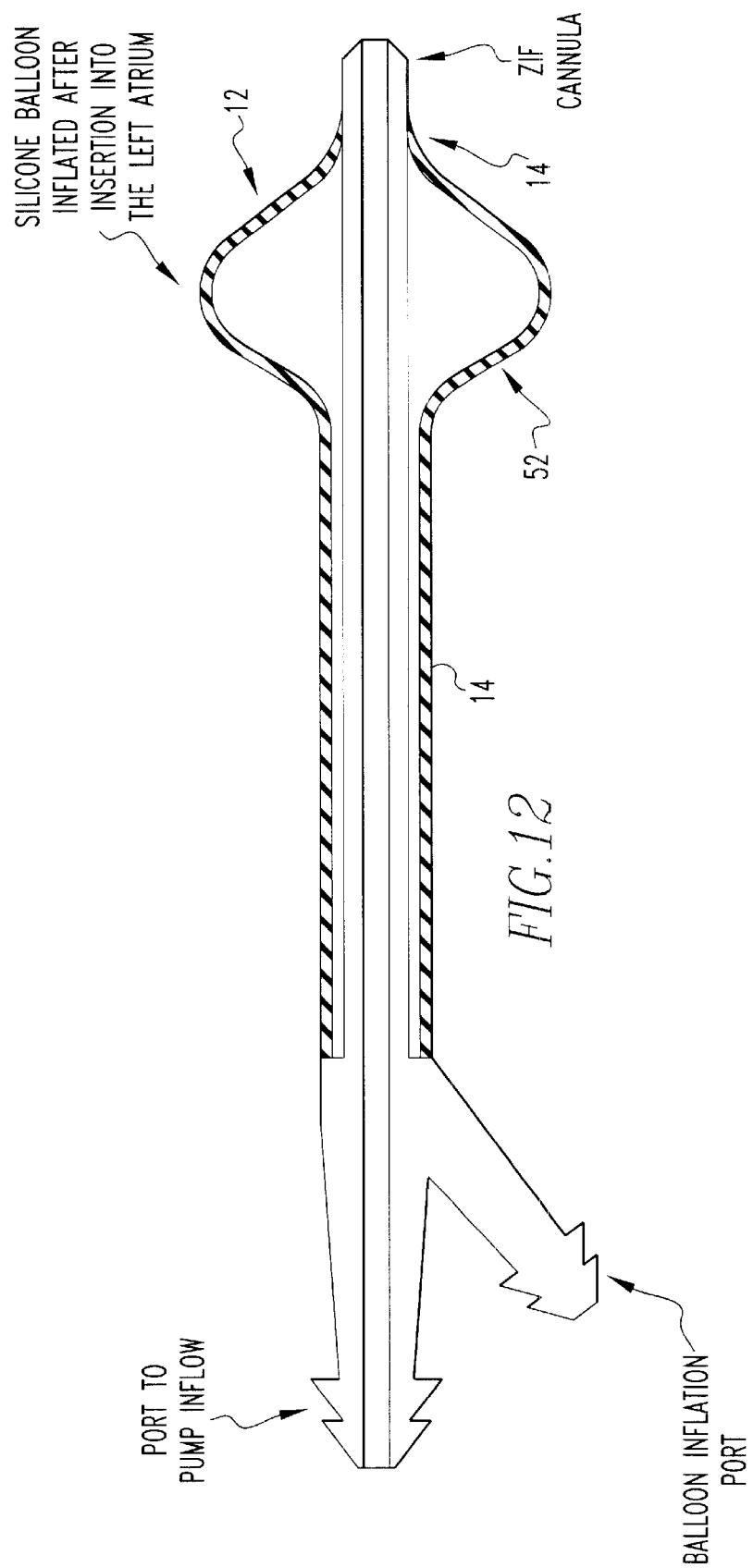
FIG. 12 is a schematic representation of an alternative embodiment of a balloon catheter at the proximal end of the cannula.

Once the orifice 18 is positioned in the left atrium and the port 20 of the cannula 12 is positioned in the right atrium, a balloon 52 disposed adjacent the orifice 18 is inflated with saline, as shown in FIG. 6, which travels along an inflation tube 54 that runs the length of the cannula 12 along the outside of the cannula 12 to a saline supply 87 disposed outside of the patient. The inflated balloon 52 serves to prevent the distal end 14 of the cannula from puncturing an atrium wall 50 of the left atrium where the distal end 14 of the cannula is now disposed, for instance when the patient is being turned or moved. The inflated balloon 52 also serves to prevent the cannula 12 from slipping back 46 into the right atrium at undesired times, such as when the patient is being turned or moved about. The balloon 52 can be deflated by removing the saline that has been introduced into it through the inflation tube 54, back out of the inflation tube 54 with negative pressure applied to the end of the inflation tube 54 extending externally from the patient. In another embodiment of a balloon 52 with the cannula 12, as shown in FIG. 12, the balloon 52 is disposed at the distal end 14 of the cannula 12.

Figure 7:
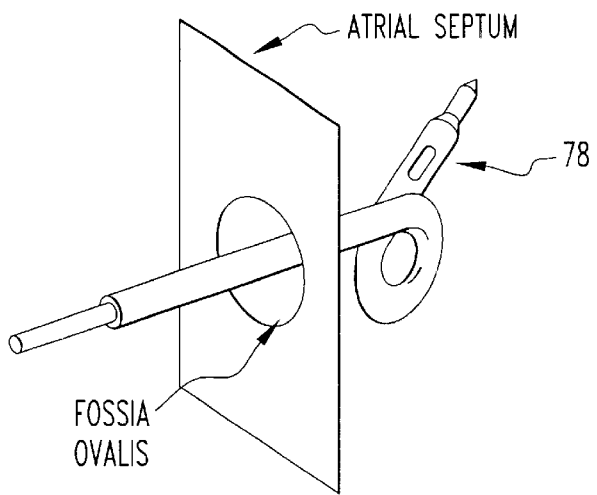
FIG. 7 is a schematic representation of a pigtail cannula.
Figure 8:
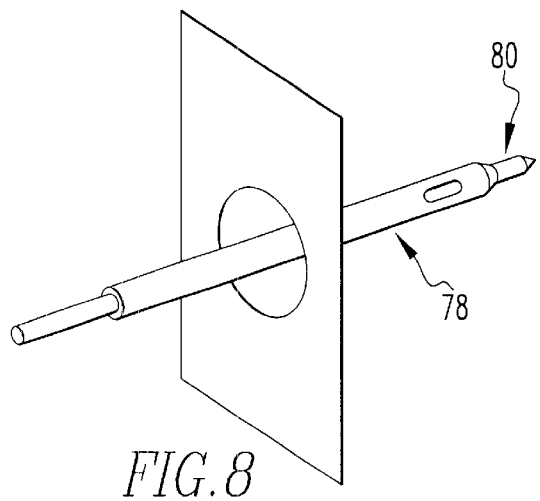
FIG. 8 is a schematic representation of a pigtail cannula with a straightening dilatory.

Alternatively, a pigtail cannula 78, as shown in FIG. 7, can be used which has its distal end curling about. As long as a straightening dilator 80 or needle 58 is present in the pigtail cannula 78, the pigtail cannula 78 is straight, as shown in FIG. 8. As soon as the dilator 80 is removed, the pigtail cannula's distal end curls about to achieve the same results as the inflated balloon 52.

A panel 24 covers over and closes the port 20 in the cannula 12 adjacent the distal end 14 of the cannula 12. The panel 24 is held in place by a frame 28 that is attached to the outside of the cannula 12 about the port 20. The panel 24 is attached to a panel wire 33 at its back end 40. The panel 24 has a first marker 42 disposed at its front end 38. The panel wire 33 extends along the outside of the cannula 12 out of the patient and is connected to a wheel hub 56. When the wheel hub 56 is turned, it causes the panel wire 33 to the retracted a corresponding amount to the movement of the wheel hub 56 and causes the panel 24 to be moved back 46 along the frame 28 away from the distal end 14. This causes the port 20 to be revealed. By continuously turning the wheel hub 56, the panel 24 is retracted from the port 20, completely revealing the port 20. If the port 20 is desired to be revealed only a portion, then the wheel hub 56 is rotated a corresponding amount to the degree that the port 20 is desired to be revealed. The first marker 42 disposed at the front end 38 of the panel 24 allows the technician to see where the front end 38 of the panel 24 is relative to a front port marker 49 that is disposed at the front 44 of the port 20. When the panel 24 completely covers and closes the port 20, the first marker 42 disposed at the front end 38 of the panel 24 aligns with the front port marker 49 disposed at the front 44 of the port 20, indicating to a technician with the imaging device that the port 20 is properly in the closed position. Along the length of the port 20, there can be gradations which are also marked to be identified with the imaging device so that the exact position of the front end 38 of the panel 24 can be identified relative to the length of the port 20 while the cannula 12 is disposed in the heart of the patient. When the port 20 is desired to be closed, the wheel hub 56 is turned in the opposite direction until the port 20 in closed behind the panel 24.

Figure 9:
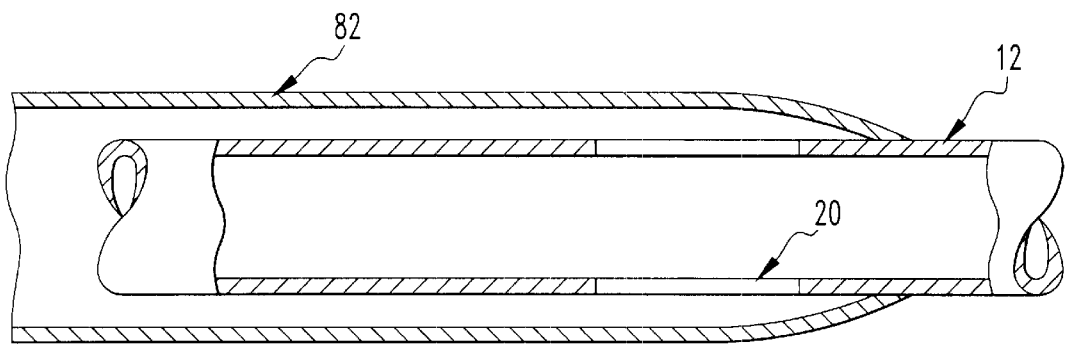
FIG. 9 is a schematic representation of a transseptal sheath over the port of a cannula.
Figure 10:
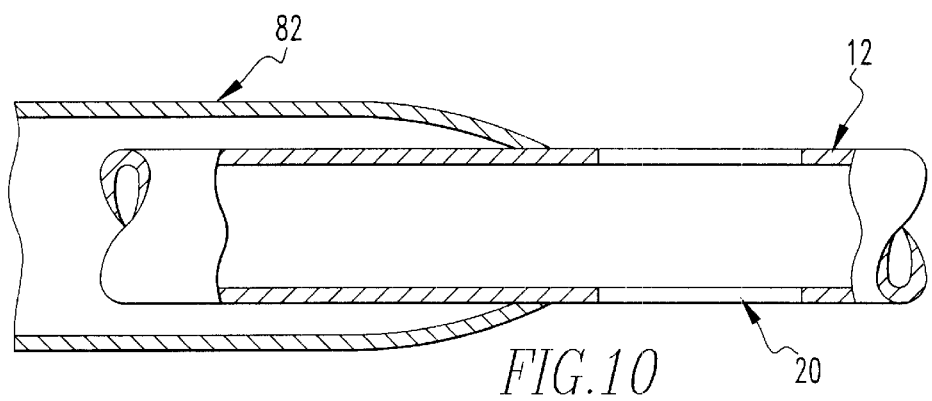
FIG. 10 is a schematic representation of the transseptal sheath retracted from the port of the cannula.

Alternatively, a transseptal sheath 82 positioned about the cannula 12 can be used instead of the panel 24, as shown in FIG. 9. When the transseptal sheath 82 is in a closed position, it covers over the port 20 so no blood can pass through the port 20. When the transseptal sheath 82 is in an open position, meaning it has been retracted by being pulled on from outside the patient, the transseptal sheath 82 has moved away from the distal end 14 exposing the port 20, as shown in FIG. 10. The extent the transseptal sheath 82 has been retracted determines how much of the port 20 is exposed. The transseptal sheath 82 can also have a marker at its end, and the cannula 12 can have gradations which are marked to identify where the end of the transseptal sheath 82 is relative to the cannula 12.

Holes 32 having an elongate shape and disposed essentially in parallel with the axis of the cannula 12 and between the orifice 18 and the port 20 further facilitates movement of blood into and out of the cannula 12. The elongate shape of the holes 32 minimizes damage to the cellular structure of the blood cells as they pass through the holes 32. Furthermore, all openings, such as the orifice 18 and the port 20, and the frame 28 are made as smooth as possible and are made of bio-inert materials such as plastic or steel to minimize or preclude the clotting of blood. In this way, access to the left and right atriums of the patient is achieved for whatever purpose, such as the attachment of a pump to the cannula 12.

Figure 11:
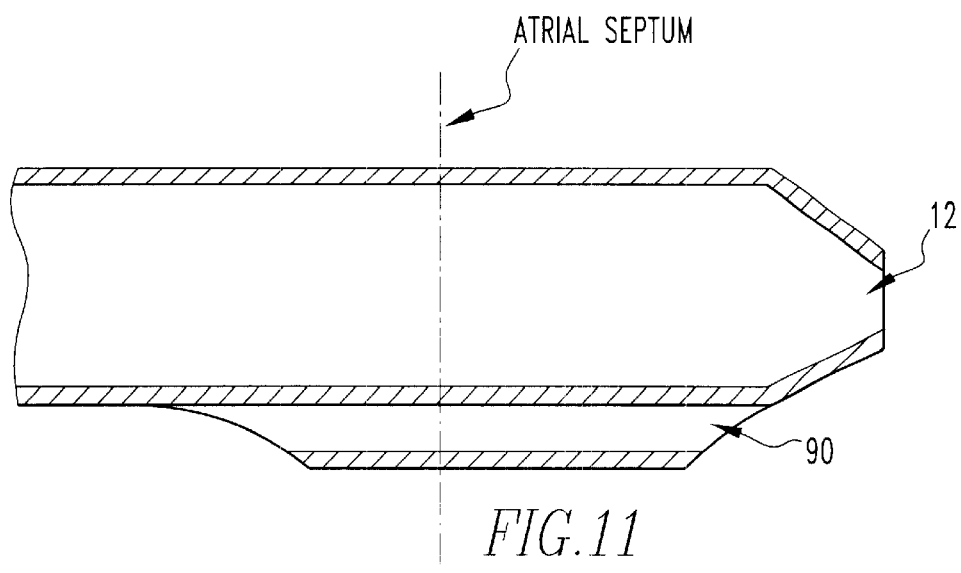
FIG. 11 is a schematic representation of an alternative cannula.

In an alternative embodiment, and referring to FIG. 11, the cannula 12 has a right atrial access lumen 90. The lumen 90 is disposed on the side on the outside surface of the cannula 12. The cannula 12 can be advanced so the lumen 90 can be disposed, entirely in the left atrium or pulled back to access the right. atrium.

The presence of the port 20 in the right atrium allows for right atrium assist. That is, blood can be removed from the right atrium to lessen the load on the right atrium. The blood from the right atrium is mixed with the blood drawn from the left atrium through the orifice 18 and holes 32 which has been fully oxygenated. Up to a mixture of 80 percent left atrium blood and 20 percent right atrium blood pumped back into the patient should not be detrimental to the patient. The degree of mixing is controlled by how much of the port 20 is open. By the clinician varying the location of the panel 24, the clinician varies the amount of blood being drawn from the right atrium and thus the mixture percentage.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for treating a patient comprising the steps of:
   inserting a catheter in a vessel; and
   moving a panel disposed in a frame positioned about a port on the catheter to open a port in the catheter disposed adjacent an orifice in the distal end of the catheter so blood can flow through the port and the orifice.

2. A method as described in claim 1 wherein the inserting step includes the step of inserting the distal end of the catheter with the orifice into the right atrium while the port is disposed in the left atrium.

3. A method as described in claim 2 wherein the inserting step includes the Step of imaging a marker about the orifice on the catheter to identify the location of the orifice in the patient.

4. A method for treating a patient comprising the steps of:
   inserting a catheter in a vessel; and
   advancing a distal end of the catheter with an orifice into the left atrium of the patient while a port in the catheter is disposed in the right atrium; and
   drawing blood through the catheter from the port in the right atrium to provide right atrium assist and from the orifice in the left atrium.

5. A method as described in claim 4 including the step of pumping the blood from the catheter back into the patient.

6. A method as described in claim 5 includes the step of moving a panel in movable attachment to the catheter about the port to open the port so blood can be drawn into the catheter through the port.

7. A method as described in claim 6 wherein the moving step includes the step of moving the panel disposed in a frame positioned about the port on the catheter.

8. A method as described in claim 7 wherein the moving step includes the step of moving a panel wire connected to the panel and extending along the catheter which causes the panel to move.

9. A method as described in claim 8 including the step of imaging an end marker disposed about the orifice to identify where the orifice is located.

10. A method as described in claim 9 including the step of imaging a first marker disposed at a front end of the panel to identify where the panel is located.

11. A method as described in claim 10 including the step of imaging a first port marker disposed at a front end of the port to identify where the port is located.

12. A method as described in claim 11 including the step of expanding a stop disposed at the distal end of the catheter when the orifice is disposed in the left atrium to prevent the catheter from puncturing an atrium wall or retracting from the left atrium.

13. A method as described in claim 12 wherein the drawing step includes the step of drawing up to 20% blood from the right atrium and at least 80 percent blood from the left atrium.

* * * * *